(12) United States Patent
Yang et al.

(10) Patent No.: US 11,395,815 B2
(45) Date of Patent: Jul. 26, 2022

(54) COMPOUND FOR TREATING OSTEOARTHRITIS

(71) Applicants: Ascentage Pharma (Suzhou) Co., Ltd., Suzhou (CN); Ascentage Pharma Group Corp Limited, Hong Kong (CN)

(72) Inventors: Dajun Yang, Suzhou (CN); Yifan Zhai, Suzhou (CN); Douglas Dong Fang, Suzhou (CN); Saijie Zhu, Suzhou (CN)

(73) Assignees: ASCENTAGE PHARMA (SUZHOU) CO., LTD., Suzhou (CN); ASCENTAGE PHARMA GROUP CORP LIMITED, Hong Kong (CN)

( * ) Notice: Subject to any disclaimer, the term of this patent is extended or adjusted under 35 U.S.C. 154(b) by 158 days.

(21) Appl. No.: 16/828,558

(22) Filed: Mar. 24, 2020

(65) Prior Publication Data

US 2020/0222366 A1 Jul. 16, 2020

Related U.S. Application Data

(63) Continuation of application No. PCT/CN2019/123919, filed on Dec. 9, 2019.

(30) Foreign Application Priority Data

Dec. 14, 2018 (WO) ............... PCT/CN2018/121120

(51) Int. Cl.
*A61K 31/407* (2006.01)
*A61P 19/02* (2006.01)
*A61K 9/00* (2006.01)

(52) U.S. Cl.
CPC .......... *A61K 31/407* (2013.01); *A61K 9/0014* (2013.01); *A61K 9/0019* (2013.01); *A61P 19/02* (2018.01)

(58) Field of Classification Search
CPC .................................... A61K 31/407
USPC ......................................... 514/409
See application file for complete search history.

(56) References Cited

U.S. PATENT DOCUMENTS 9,745,314 B2 * 8/2017 Wang ............... A61P 35/00
9,993,472 B2 * 6/2018 Laberge .............. A61K 45/06

FOREIGN PATENT DOCUMENTS

WO WO 2015/161032 A1 10/2015
WO WO 2017/176957 A1 10/2017

OTHER PUBLICATIONS

Aguilar et al., "Discovery of 4-((3'R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido)bicyclo[2.2.2]octane-1-carboxylic Acid (AA-115/APG-115): A Potent and Oral Active Murine Double Minute 2 (MDM2) Inhibitor in Clinical Development," *J. Med. Chem.*, 60(7): 2819-2839 (2017).

* cited by examiner

*Primary Examiner* — Nizal S Chandrakumar
(74) *Attorney, Agent, or Firm* — Jones Day

(57) ABSTRACT

The present invention relates to a compound for treating or preventing osteoarthritis. The compound relieves the joint pain, inhibits and attenuates the development of post-traumatic osteoarthritis in mouse model. The present invention also provides a pharmaceutical composition comprising the compound for treating or preventing osteoarthritis. The present invention further provides a method for treating or preventing osteoarthritis by administrating to the patient in need thereof with the pharmaceutical composition.

14 Claims, 1 Drawing Sheet

COMPOUND FOR TREATING OSTEOARTHRITIS

CROSS REFERENCE TO RELATED APPLICATIONS

This application is a continuation of International Application No. PCT/CN2019/123919, filed Dec. 9, 2019; which claims the benefit of International Application No. PCT/CN2018/121120, filed Dec. 14, 2018; the disclosure of each of which is incorporated herein by reference in its entirety.

FIELD OF THE INVENTION

The present invention relates to a compound for treating or preventing osteoarthritis. The compound relieves the joint pain, inhibits and attenuates the development of post-traumatic osteoarthritis in mouse model. The present invention also provides a pharmaceutical composition comprising the compound for treating or preventing osteoarthritis. The present invention further provides a method for treating or preventing osteoarthritis by administrating to the patient in need thereof with the pharmaceutical composition.

BACKGROUND OF THE ART

Osteoarthritis (OA) is the most common form of arthritis, with a prevalence after the age of 65 years of about 60% in men and 70% in women. Current treatment options for Osteoarthritis are limited. They include symptomatic treatment with simple analgesics, non-steroidal anti-inflammatory drugs (NSAIDs) or intra-articular (IA) injected glucocorticoids and hyaluronic acid (HA) preparations. Non-pharmacological measures range from physical exercise and weight loss to joint lavage, and eventually surgical joint replacement.

There are major unmet needs in Osteoarthritis treatment, for disease-modifying Osteoarthritis drugs, which are not available yet, and also for efficacious pain treatments with long-lasting effects. Furthermore, there is a significant unmet need for Osteoarthritis treatments which do not have any major side effects, due to the chronic nature of the disease often requiring treatment of extended duration. The currently available systemic drugs for relief of Osteoarthritis pain, e.g., the non-selective NSAIDs and selective cyclooxygenase 2 (COX-2) inhibitors, are effective in the early-mid stages of OA, but often fail to provide adequate pain relief as the joint deteriorates. In addition, NSAIDs cause gastrointestinal complications in a significant number of patients, and the COX-2 inhibitors have recently raised concerns regarding cardiovascular side effects/risks, resulting in the withdraw of the COX-2 inhibitors Vioxx and Bextra from the US market. Drugs for treating or preventing osteoarthritis are still required by a large amount of patients.

The object of the present invention is to provide a compound for treating or preventing osteoarthritis. Another object of the invention is to provide a pharmaceutical composition for therapeutic or prophylactic treatment of osteoarthritis. It is yet another object of the present invention to provide a method for therapeutic or prophylactic treatment of osteoarthritis.

SUMMARY OF THE INVENTION

After an intensive research, the present invention provides a compound of formula (I), including a pharmaceutically acceptable salt thereof, for treating or preventing osteoarthritis, as well as a pharmaceutical composition comprising said compound or a pharmaceutically acceptable salt thereof. The present invention also provides a method for inhibiting osteoarthritis, particularly for therapeutic or prophylactic treatment of osteoarthritis, said method comprises administrating to a patient in need thereof with a pharmaceutical composition comprising an effective amount of the compound or a pharmaceutically acceptable salt thereof.

The compound of the invention is a compound of formula (I):

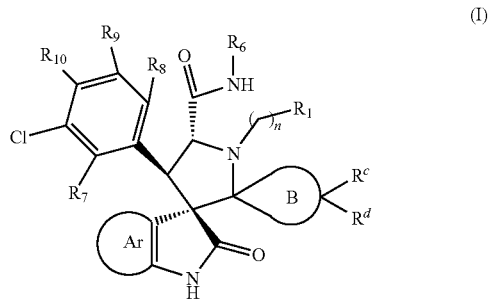

or a pharmaceutically acceptable salt thereof, wherein

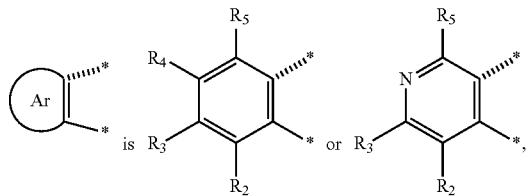

ring B is

$R_1$ is H, substituted or unsubstituted $C_{1-4}$ alkyl;
n is 0, 1, or 2;
$R_2$, $R_3$, $R_4$, $R_5$, $R_7$, $R_8$, $R_9$, and $R_{10}$, independently, are selected from the group consisting of H, F, Cl, $CH_3$, and $CF_3$;
$R_6$ is

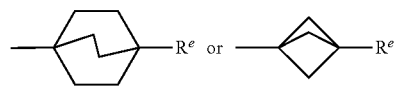

$R^a$ is hydrogen, or substituted or unsubstituted $C_{1-4}$ alkyl;
$R^b$ is hydrogen, or substituted or unsubstituted $C_{1-4}$ alkyl;
$R^c$ and $R^d$ are substituents on one carbon atom of ring B, wherein
$R^c$ is H, $C_{1-3}$ alkyl, $C_{1-3}$ alkylene $OR^a$, $OR^a$, or halo;
$R^d$ is H, $C_{1-3}$ alkyl, $C_{1-3}$ alkylene $OR^a$, $OR^a$, or halo;
$R^e$ is —C(=O)$OR^a$, —C(=O)$NR^aR^b$, or —C(=O)$NHSO_2CH_3$.

The compound of formula (I), including or a pharmaceutically acceptable salt thereof, relieves the joint pain, inhibits and attenuates the development of post-traumatic osteoarthritis in mouse model.

The compound of the present invention is a therapeutic or prophylactic agent for osteoarthritis. It can be formulated into a pharmaceutical composition for oral or parenteral administration by combining with a pharmaceutically acceptable carrier, excipient, additive, or the like. In a particular embodiment of the present invention, the pharmaceutical composition is in the dosage form for parenteral injection. In a preferable embodiment of the present invention, the pharmaceutical composition is in the dosage form for local injection of the osteoarthritis.

DETAILED DESCRIPTION OF THE INVENTION

Figure 1:
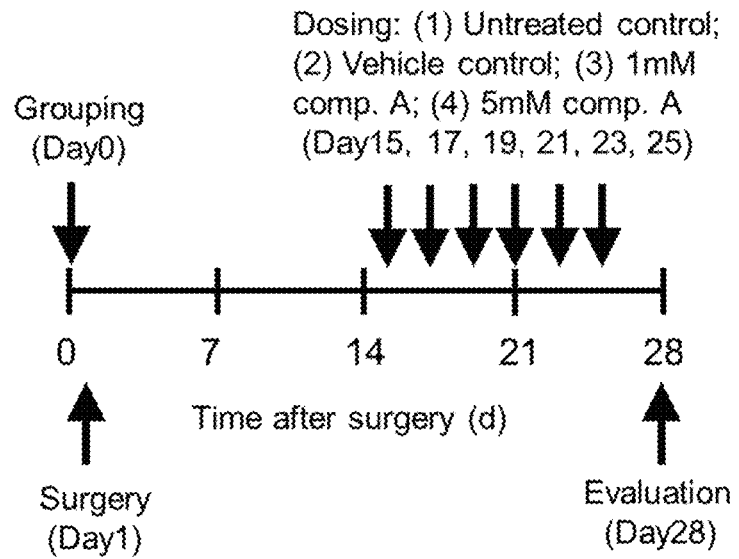
FIG. 1. Schematic of the time course for the experiment in the Assay of the activity of compound A in mouse Osteoarthritis model.

The present invention provides a compound of formula (I) or pharmaceutically acceptable salt thereof, for treating or preventing osteoarthritis. The present invention also provides a pharmaceutical composition comprising an effective amount of said compound or pharmaceutically acceptable salt thereof. The present invention further provides a method for inhibiting osteoarthritis, particularly for therapeutic or prophylactic treatment of osteoarthritis, said method comprises administrating to a patient in need thereof with a pharmaceutical composition comprising an effective amount of the compound or pharmaceutically acceptable salt thereof. According to the embodiments of the present invention, the compounds of formula (I) or pharmaceutically acceptable salt thereof relieved the joint pain, inhibited and attenuated the development of post-traumatic osteoarthritis in mouse model.

The structure of the compound of formula (I) is as follows:

(I)

The symbols of formula (I) are as defined as above.

As used herein, the term "alkyl" refers to straight chained and branched saturated C1-6 hydrocarbon groups, including but not limited to methyl, ethyl, n-propyl, i-propyl, n-butyl, sec-butyl, t-butyl, n-pentyl, 2-methylbutyl, 3-methylbutyl, 2,2-dimethylpropyl, n-hexyl, and etc.

The term "alkylene" refers to an alkyl group having a substituent. An alkyl, e.g., methyl, or alkylene, e.g. —$CH_2$—, group can be substituted with one or more, and typically one to three, of independently selected halo, trifluoromethyl, trifluoromethoxy, hydroxy, alkoxy, nitro, cyano, alkylamino, or amino groups, for example.

As used herein, the term "halo" is defined as fluoro, chloro, bromo, and iodo. The term "trifluoromethyl" is defined as —$CF_3$.

In a preferred embodiment, ring B is

In some embodiments, n is 0 or 1 and $R_1$ is H or $CH_3$.

In some embodiments, —$(CH_2)_n$—$R_1$ is H, $CH_3$, or $CH_2CH_3$.

In some embodiments, $R_2$ is H.

In other embodiments, $R_3$ is preferably Cl.

In still another embodiment, $R_4$ is H, $R_5$ is H, or both $R_4$ and $R_5$ are H.

In some preferred embodiments, $R_7$ is F.

In some preferred embodiments, each of $R_8$, $R_9$, and $R_{10}$ are H.

In some preferred embodiments, $R^a$ and $R^b$, individually, are H, $CH_3$, or $CH_2CH_3$.

In some preferred embodiments, $R^c$ and $R^d$, individually, are H, halo, OH, $CH_3$, $CH_2CH_3$, or $CH_2OH$.

In some preferred embodiments, $R^c$ and $R^d$ taken with ring B form:

In some preferred embodiments, $R^e$ is —C(=O)OH, —C(=O)$NH_2$, or —C(=O)$NHSO_2CH_3$.

In some preferred embodiments, $R^6$ is
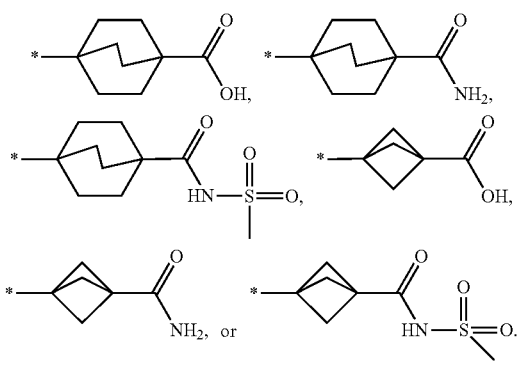
Specific compounds of the present invention include, but are not limited to, the compounds having the structures set forth below.
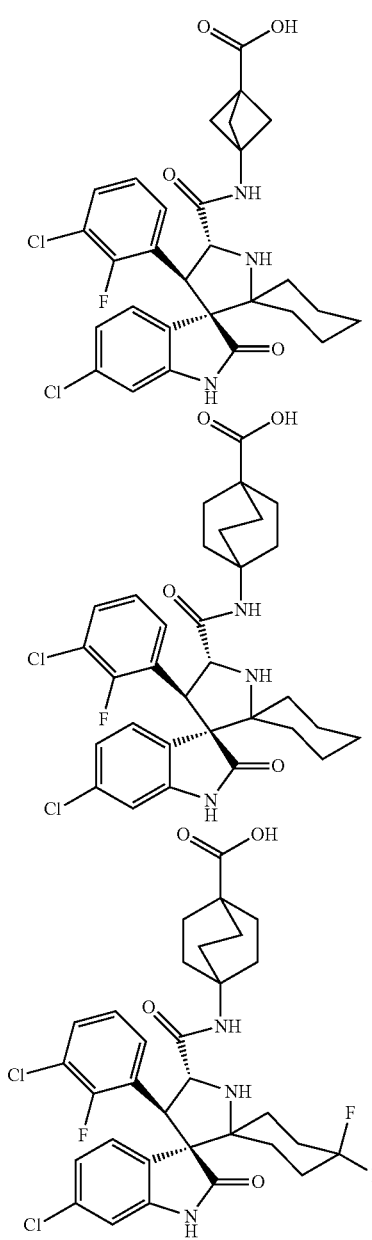
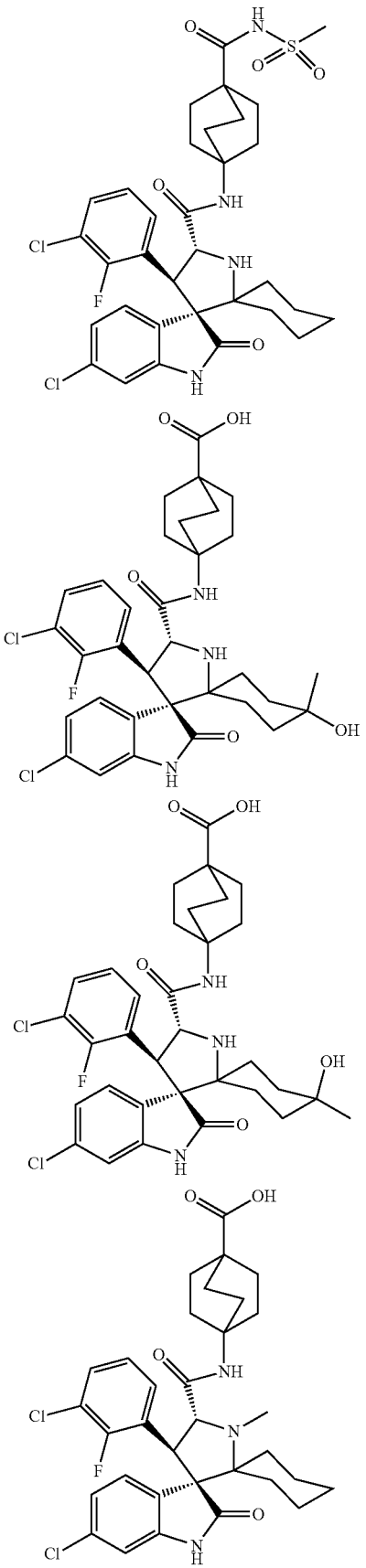

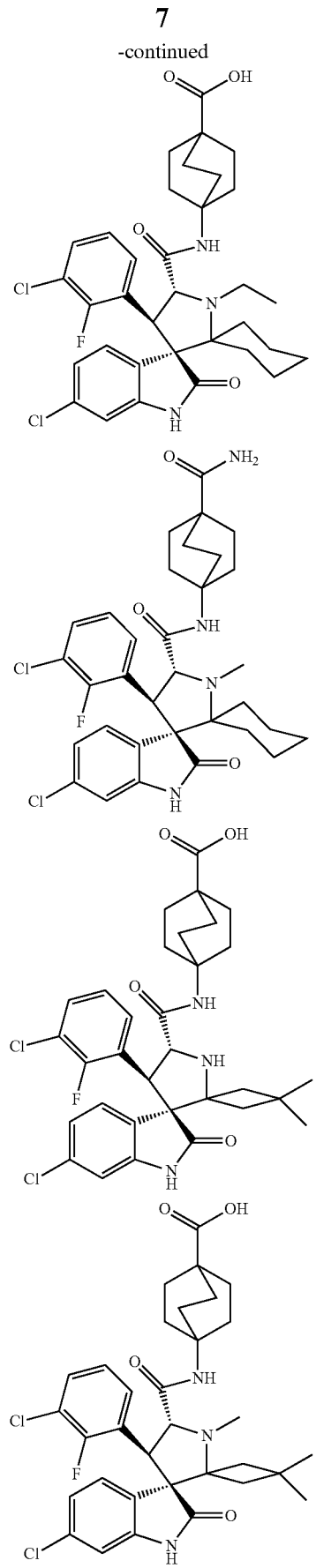
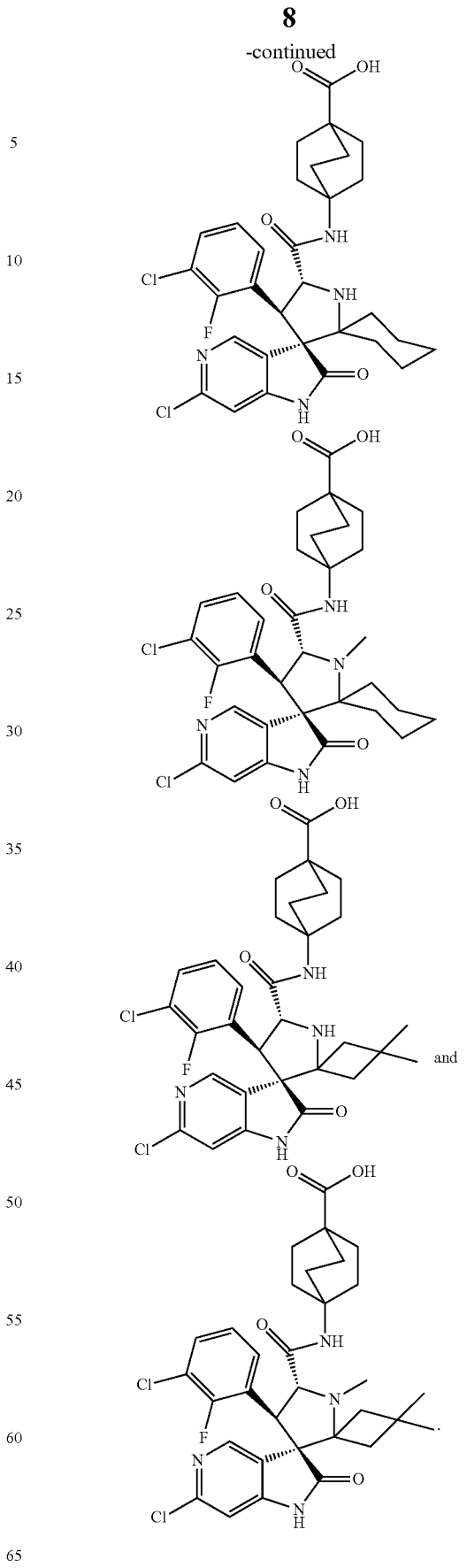
In the most preferred embodiments, the compound of the invention is compound A

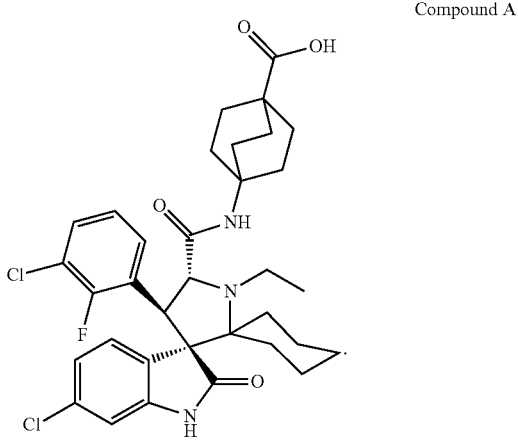 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

Compound A

Additionally, salts of the present compounds also are included in the present invention and can be used in the methods disclosed herein. The present invention further includes all possible stereoisomers and geometric isomers of the compounds of structural formula (I).

Pharmaceutically acceptable salts of the compounds of the invention often are preferred in the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid having a suitable cation, such as, but not limited to, alkali and alkaline earth metal ions, e.g., $Na^+$, $K^+$, $Ca^{2+}$, and $Mg^{2+}$ as well as organic cations such as, but not limited to, ammonium and substituted ammonium ions, e.g., $NH^{4+}$.

The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, trifluoroacetate and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, and trifluoroacetate. In light of the foregoing, any reference to compounds of the present invention appearing herein is intended to include compounds of structural formula (I) as well as pharmaceutically acceptable salts thereof.

According to the embodiments of the present invention, the compound of formula (I) relieved the joint pain, inhibited and attenuated the development of post-traumatic osteoarthritis in mouse model. In the most preferred embodiment of the present invention, the compound is compound A.

Osteoarthritis is generally classified into two categories, which are primary osteoarthritis and secondary osteoarthritis. Primary osteoarthritis is mostly related to aging. It is one of the commonly diagnosed orthopedic conditions and tends to affect individuals aged 53 and above. Secondary osteoarthritis is caused by another disease or condition. Conditions that can lead to secondary osteoarthritis include obesity, repeated trauma or surgery to the joint structures, abnormal joints at birth (congenital abnormalities), gout, diabetes, and other hormone disorders. In an embodiment of the present invention, the osteoarthritis is primary osteoarthritis, or secondary osteoarthritis.

The osteoarthritis may also be classified as osteoarthritis of weight-bearing joints and osteoarthritis of non-weight-bearing joints. In an embodiment of the present invention, the osteoarthritis is osteoarthritis of weight-bearing or non-weight-bearing joints. In further embodiments of the present invention, the osteoarthritis is selected from the group of gonarthrosis, coxarthrosis, foot osteoarthritis and spinal osteoarthritis, shoulder osteoarthritis, elbow osteoarthritis, hand osteoarthritis, and temporomandibular arthrosis. In particular embodiments of the present invention, the osteoarthritis is osteoarthritis of weight-bearing joints, such as gonarthrosis in the knee joint, coxarthrosis in the hip joint, foot osteoarthritis in the foot and spinal osteoarthritis in the spine. In particular embodiments of the present invention, the osteoarthritis is post-traumatic osteoarthritis.

The terms "treatment," "method for treating" and "therapeutic treatment," as used herein, mean eliminating, inhibiting or relieving the symptoms of a patient with arthritis according to the present invention, or methods or drugs for that purpose. In addition, the terms "prevention" and "prophylactic treatment" mean preventing arthritis or drugs for that purpose.

The compound of the present invention is a therapeutic or prophylactic agent for osteoarthritis. It can be formulated into a pharmaceutical composition for oral or parenteral administration by combining with a pharmaceutically acceptable carrier, excipient, additive, or the like. In a particular embodiment of the present invention, the pharmaceutical composition is in the dosage form for parenteral injection. In a preferable embodiment of the present invention, the pharmaceutical composition is in the dosage form for local injection of the osteoarthritis.

Examples of injection formulations include sterile aqueous or non-aqueous solutions, suspensions, and emulsions for injection. The pharmaceutical composition of the invention may further contain adjuvants, such as preservatives, emulsifiers, dispersants, stabilizers, and dissolution auxiliary agents. The above-described components may be sterilized by conventional sterilization methods. The injections may be liquid preparations, or freeze-dried preparations that may be reconstituted before use. The preferred injection formulation is administered by subcutaneous, intramuscular, percutaneous and intra-articular injection. In the most preferred embodiment of the present invention, the injection is formulation is administered by intra-articular injection.

The local administration of the compound into the articular will provide a few advantages in the treatment of osteoarthritis. First, the intra-articular injection would insure the local high concentration of the compound and alleviate the disease condition. Second, local injection of the compound would avoid or at least partially avoid the systemic exposure of the compound, thus potentially mitigate the systemic side effects.

The present invention further relates to a pharmaceutical composition for treating or preventing osteoarthritis, said composition comprising a therapeutic or prophylactic effective amount of the compound of formula (I) or pharmaceutically acceptable salt thereof, and pharmaceutically acceptable carrier, excipient, additive, or the like.

The present invention further relates to the use of a compound in the manufacture of a medicament for treating or preventing osteoarthritis, the compound is a compound of formula (I) or pharmaceutically acceptable salt thereof.

In a preferred embodiment, said medicament is in the dosage form for local delivery, which is to be administrated topically or to be administrated via intraarticular injection of the osteoarthritis. The medicament is for the treatment of weight-bearing joints, preferably selected from gonarthrosis in the knee joint, coxarthrosis in the hip joint, foot osteoarthritis in the foot and spinal osteoarthritis in the spine. Particularly, said medicament is for the treatment of post-traumatic osteoarthritis.

The compounds of formula (I) or a pharmaceutically acceptable salt thereof can be obtained according to the preparation methods described in WO2015/161032A1, published on Oct. 22, 2015, which is incorporated herein by reference, or a method analogous thereto.

An effective amount of the compounds of formula (I) required for use in therapeutic or prophylactic treatment varies with the nature of the condition being treated, the length of time that activity is desired, and the age and the condition of the patient, and ultimately is determined by the attendant physician. Dosage amount and intervals can be adjusted individually to provide plasma levels of the compound that are sufficient to maintain the desired therapeutic effects. The desired dose can be administered conveniently in a single dose, or as multiple doses administered at appropriate intervals, for example as one, two, three, four or more sub-doses per day. Multiple doses are often desired or required. For example, compound A can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

In a preferred embodiment, the compound of the invention is prepared into a formulation for local delivery. The formulation may be administered to a patient in need thereof topically or be administered via intraarticular injection. For local delivery, the compound can be present at a concentration of about 0.01 to 100 mg per gram of carrier. In a one embodiment, the compound is present at a concentration of about 0.1-10 mg/ml.

The pharmaceutical compositions provided herein can be administered to any patient which may experience the beneficial effects of the compound. Foremost among such patients are mammals, e.g., humans, although the methods and compositions provided herein are not intended to be so limited. Other patients include veterinary animals (cows, sheep, pigs, horses, dogs, cats and the like). The dosage administered will be dependent upon the age, health, and weight of the recipient, kind of concurrent treatment, if any, frequency of treatment, and the nature of the effect desired.

The present invention will be described in more detail by the following examples, which are for illustrative purposes only and are not intended to limit the scope of the invention. Thus, the present invention is not limited to those examples.

EXAMPLES OF THE INVENTION

Preparation Examples: Preparation of the Exemplified Compounds

The exemplified compounds of the present invention are prepared as follows. The following synthetic scheme is representative of the reactions used to synthesize the compounds. Modifications and alternate schemes to prepare the compound of the invention are readily within the capabilities of persons skilled in the art by substitution of the appropriate reagents and agents in the syntheses shown below.

Solvents and reagents were obtained commercially and used without further purification. Chemical shifts (δ) of NMR spectra are reported as δ values (ppm) downfield relative to an internal standard, with multiplicities reported in the usual manner. Unless otherwise stated all temperatures are in degrees Celsius.

Compounds of formula (I) can also be prepared by asymmetric synthetic methods, as described in U.S. Pat. Nos. 7,759,383 and 7,737,174 (each incorporated herein by reference), and Ding et al., J. Am. Chem. Soc. 127: 10130-10131 (2005)). In the case of an asymmetric synthesis, compounds of structural formula (I) can be separated by chiral resolution methods well known in the art, e.g., chiral column chromatography. Suitable chiral columns for use in chiral resolutions include, for example, Daicel CHIRAL-CEL® OD-H, Daicel CHIRAKPAK® AD-H, and Regis Technologies ULMO chiral columns. Other chiral resolution methods are also possible.

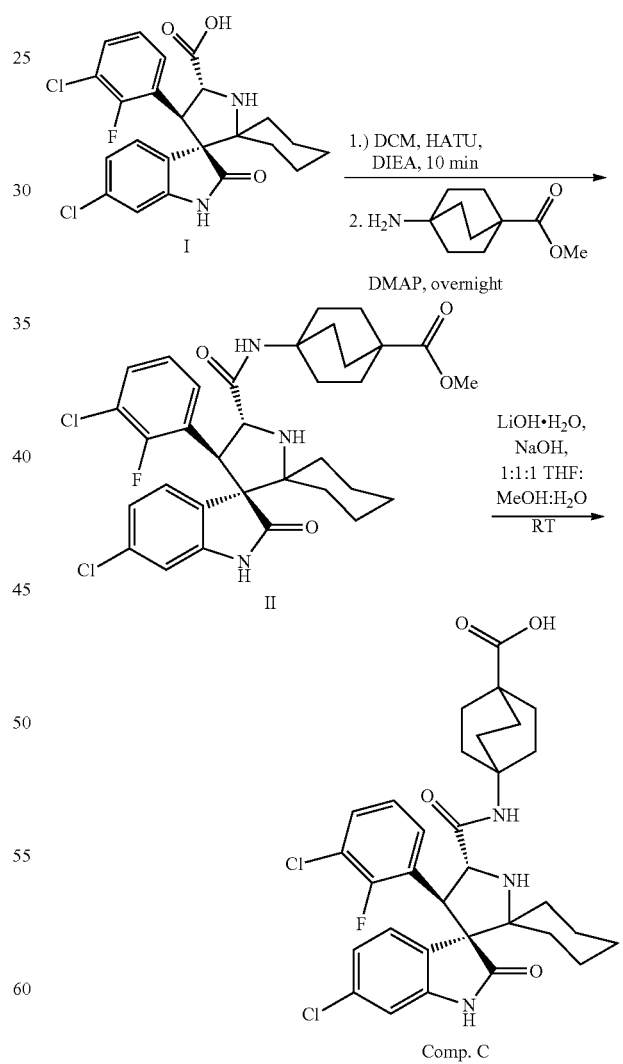

Preparation of Compound C:
[Bis(dimethylamino)methylene]-1H-1,2,3-triazolo[4,5-b]pyridinium 3-oxide hexafluorophosphate (HATU) (616 mg, 1.62 mmol), N,N-diisopropylethylamine (0.550 mL, 3.24 mmol) were added to a suspension of acid compound I (500 mg, 1.08 mmol) in dichloromethane (DCM) (15 ml) and stirred. After 10 minutes, methyl 4-aminobicyclo[2.2.2]octane-1-carboxylate (396 mg, 2.16 mmol) and 4-dimethylaminopyridine (132 mg, 1.08 mmol) were added to the reaction. After overnight, the solvent was removed in vacuo and the crude was purified by column chromatography to give 549 mg of intermediate II.

LiOH.H$_2$O (110 mg, 2.62 mmol) and sodium hydroxide (105 mg, 2.62 mmol) were added to a solution of intermediate II (549 mg, 0.873 mmol) dissolved in a mixture of tetrahydrofuran (THF) (3 mL), H$_2$O (3 mL), and MeOH (3 mL). After the hydrolysis was complete, as determined by thin layer chromatography (TLC), the reaction was quenched with trifluoroacetic acid (TFA) (3 mL) and stirred. After 5 minutes, the solution was concentrated in vacuo (not to dryness) and the resulting oil was re-dissolved in CH$_3$CN and H$_2$O (1:1) and the solution was purified by preparative HPLC. The purified fractions were combined, concentrated in vacuo, re-dissolved in H$_2$O, frozen and lyophilized to give Compound C (TFA salt) as a white powder.

Compound C: $^1$H-NMR (300 MHz, CD$_3$OD) δ ppm 7.63 (t, J=6.84 Hz, 1H), 7.45 (d, J=6.76 Hz, 1H), 7.35 (t, J=7.21 Hz, 1H), 7.18-7.04 (m, 2H), 6.77 (dd, J=1.26 Hz, 1H), 4.68 (d, J=10.61 Hz, 1H), 2.73-2.48 (m, 1H), 2.16-1.98 (m, 1H), 1.98-1.43 (m, 18H), 1.27-1.02 (m, 2H); ESI-MS m/z 614.92 (M+H)$^+$.

Preparation of Compound B:

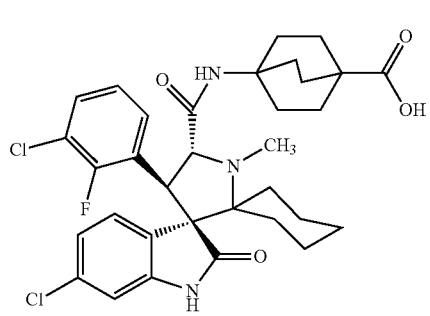

Compound B

Paraformaldehyde (15 mg, 0.506 mmol) was added to a solution of compound C (20 mg, 0.028 mmol) dissolved in AcOH (1 mL). After 15 minutes sodium triacetoxyborohydride (59 mg, 0.28 mmol) was added and after reacting overnight the reaction was quenched with saturated ammonium chloride solution and extracted with ethyl acetate. The ethyl acetate solvent was removed in vacuo and the resulting oil was re-dissolved in a solution of acetonitrile and water (1:1 with 0.1% TFA) and purified by preparative HPLC. The pure compound B fractions were combined, concentrate in vacuo, re-dissolved in water (with minimum amount of acetonitrile), frozen and lyophilized to give compound B (TFA salt) as a white powder.

Compound B: $^1$H-NMR (300 MHz, CD$_3$OD) δ ppm 7.94 (s, 1H), 7.61-7.52 (m, 2H), 7.40 (t, J=7.32 Hz, 1H), 7.19-7.08 (m, 2H), 6.78 (d, J=1.56 Hz, 1H), 4.99 (d, J=11.86 Hz, 1H), 4.63 (d, J=12.06 Hz, 1H), 3.27 (s, 3H), 2.61-2.48 (m, 1H), 2.32-2.14 (m, 2H), 1.88-1.40 (m, 18H), 1.37-1.12 (m, 1H); ESI-MS m/z 628.83 (M+H)$^+$.

Preparation of Compound A:

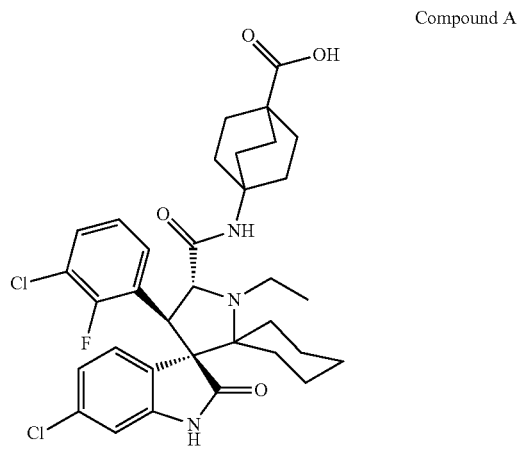 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

Compound A

Chemical Formula: C$_{34}$H$_{38}$Cl$_2$FN$_3$O$_4$ Exact Mass: 641.22 Molecular Weight: 642.59.

Compound A was obtained using the same synthetic strategy described for Compound B.

Compound A: $^1$H-NMR (300 MHz, CD$_3$OD) δ ppm 7.63 (t, J=7.04 Hz, 1H), 7.56-7.48 (m, 2H), 7.42 (t, J=7.39 Hz, 1H), 7.18 (t, J=7.96 Hz, 1H), 7.10 (d, J=8.06 Hz, 1H), 6.79 (s, 1H), 5.08-4.96 (m, 1H), 4.57 (d, J=11.85 Hz, 1H), 4.18-3.99 (m, 1H), 3.87-3.69 (m, 1H), 2.70-2.54 (m, 1H), 2.36-2.13 (m, 2H), 1.94-1.45 (m, 18H), 1.39 (t, J=6.65 Hz, 3H), 1.32-1.14 (m, 1H); ESI-MS m/z 642.50 (M+H)$^+$.

Assay Example: Assay of the Activity of the Compound in Mouse Osteoarthritis Model C57BL/6 mice aged 10 weeks were used for the study (n=12 for each group). Anterior cruciate ligament transection (ACLT) model was used to simulate the pathological condition in OA. To conduct ACLT surgery, the joint capsule of the right rear limb of mice was opened, and the anterior cruciate ligament (ACL) was transected with micro-scissors under a surgical microscope. After irrigation with saline to remove tissue debris, the skin incision was closed.

Fourteen days after surgery, mice were treated according to the regimen shown in Table 1 and FIG. 1.

TABLE 1

Description of different treatment groups

| Group | Formulation | Injection route | Injection volume | Dose |
|---|---|---|---|---|
| 1. Untreated control | Untreated control | No injection | No injection | 0 |
| 2. Vehicle control | 5% Pluronic F68 in PBS7.4 | Intraarticular | 10 uL | 0 |
| 3. 1 mM comp. A | 1 mM in 5% Pluronic F68 in PBS7.4 | Intraarticular | 10 uL | 0.01 μmol |
| 4. 5 mM comp. A | 5 mM in 5% Pluronic F68 in PBS7.4 | Intraarticular | 10 uL | 0.05 μmol |

Blank vehicle contained 5% Pluronic F68 (BASF, Germany) in 10 mM phosphate buffered saline (PBS, NaH$_2$PH$_4$/

Na$_2$HPO$_4$) with pH adjusted to 7.4. Before each injection and sacrificing at the end point, the function of the limbs was assessed by a weight bearing test. All the mice were sacrificed for pathological evaluation and immunohistochemical staining 13 days after first dosing.

Weight bearing test was conducted using a plethysmometer model 600MR (IITC Life Science, CA, USA). Briefly, after calibration of the equipment, mice were placed inside the chamber to stand with each hind paw on a scale, allowed to stand for 5-10 s until the readings were stable. The readings reflected the weight that was placed on each hind limb. The ACLT surgery caused osteoarthritis (OA) and decreased the weight placed on the hind limb. The results were expressed as the percentage of the weight placed on the operated limb versus the contralateral unoperated limb (weight bearing %). Weight bearing results 13 days after first dose following different treatment were shown in FIG. 2.

The value of weight bearing % is expected to be 100 in healthy mice, indicating the same weight placed on both limbs. The value of weight bearing % will decrease to 50~60 after ACLT surgery due to less weight that could be placed on the operated limb than the unoperated limb. Alleviation of joint pain by Osteoarthritis should be reflected by an increased value of weight bearing %.

Figure 2:
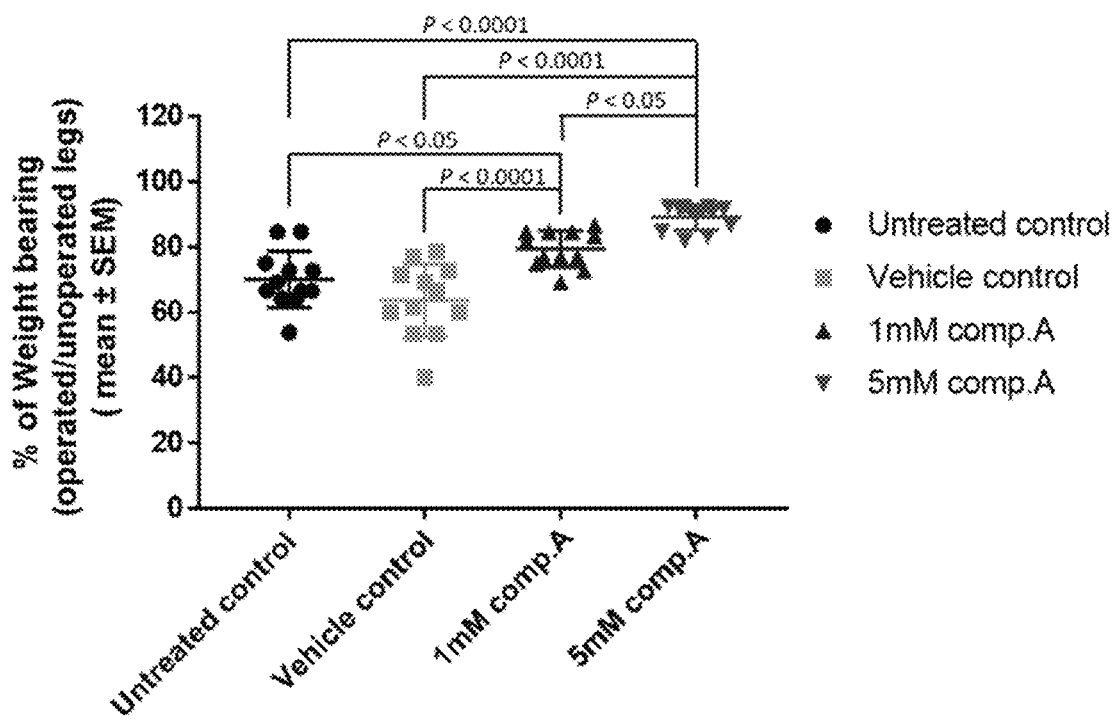
FIG. 2. The percentage of weight placed on the operated limb versus the contralateral control (left) of mice 13 days after first dose following different treatment, in the Assay of the activity of compound A in mouse Osteoarthritis model.
 Weight bearing %: weight bearing of operated leg/unoperated leg (indicator of joint pain);
 Weight bearing %=100: in healthy mice, same bearing in both legs;
 Weight bearing %<100: decrease to 50~60 after anterior cruciate ligament transection (ACLT);
 Increased Weight bearing %: indicated relieved joint pain.

As seen in FIG. 2, no significant difference was observed between untreated control group and vehicle control group (P>0.05), indicating no therapeutic effect of the blank vehicle. On the other hand, intra-articular injection of compound A showed a dose-dependent effect in improving weight bearing %, indicating its effect in alleviating the pain caused by OA. It should be noted that 0.01 µmol of compound A already showed therapeutic effect, which was reflected in the significantly increased value of weight bearing % compared with untreated control (P<0.05) and vehicle control (P<0.0001). Further increasing the dose to 0.05 µmol resulted in a further increase in the value of weight bearing % (P<0.05 vs 1 mM compound A group), indicating an even stronger therapeutic effect.

It proved that, compound A significantly relieved the joint pain in mouse ACLT model.

Mouse joints were fixed in 4% paraformaldehyde overnight, dehydrated in increasing concentrations of ethanol and embedded in paraffin. Sections (5 µm) were cut from the paraffin blocks and applied to glass slides. The sections were stained for proteoglycans with aqueous safranin O (0.1%) for 5 min, and the specimens were then mounted.

Pathological changes in the structure and/or appearance of the subchondral bone could be observed in the joint of mouse from the untreated control and vehicle control group. On the other hand, these pathological changes including articular cartilage erosion, proteoglycan loss and the thinning and calcification of articular cartilage were attenuated after treatment with compound A. It proved that, compound A increased cartilage development and created a pro-chondrogenic environment.

What is claimed:

1. A method for treating osteoarthritis, comprising administrating to a patient in need thereof a therapeutically effective amount of compound A or a pharmaceutically acceptable salt thereof:

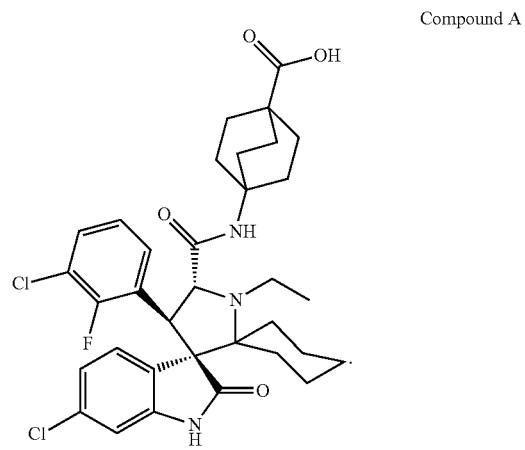 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

Compound A

2. The method of claim 1, wherein the compound is administrated topically.

3. The method of claim 1, wherein the osteoarthritis is primary osteoarthritis.

4. The method of claim 1, wherein the osteoarthritis is gonarthrosis.

5. The method of claim 1, wherein the osteoarthritis is post-traumatic osteoarthritis.

6. The method of claim 1, wherein the compound is administrated via intra-articular injection.

7. The method of claim 1, wherein the osteoarthritis is secondary osteoarthritis.

8. The method of claim 1, wherein the osteoarthritis is coxarthrosis.

9. The method of claim 1, wherein the osteoarthritis is foot osteoarthritis.

10. The method of claim 1, wherein the osteoarthritis is spinal osteoarthritis.

11. The method of claim 1, wherein the osteoarthritis is shoulder osteoarthritis.

12. The method of claim 1, wherein the osteoarthritis is elbow osteoarthritis.

13. The method of claim 1, wherein the osteoarthritis is hand osteoarthritis.

14. The method of claim 1, wherein the osteoarthritis is temporomandibular arthrosis.

* * * * *